United States Patent
Shang et al.

(10) Patent No.: US 9,295,486 B2
(45) Date of Patent: Mar. 29, 2016

(54) DISPOSABLE CIRCUMCISION CLAMP

(76) Inventors: Jianzhong Shang, Wuhu (CN); Jingjing Shang, Wuhu (CN)

(*) Notice: Subject to any disclaimer, the term of this patent is extended or adjusted under 35 U.S.C. 154(b) by 0 days.

(21) Appl. No.: 13/814,481

(22) PCT Filed: Aug. 19, 2011

(86) PCT No.: PCT/CN2011/001386
§ 371 (c)(1),
(2), (4) Date: Feb. 5, 2013

(87) PCT Pub. No.: WO2012/022125
PCT Pub. Date: Feb. 23, 2012

(65) Prior Publication Data
US 2013/0138116 A1    May 30, 2013

(30) Foreign Application Priority Data
Aug. 20, 2010   (CN) ............ 2010 2 0299303 U

(51) Int. Cl.
*A61B 17/32*    (2006.01)
*A61B 17/326*   (2006.01)
*A61B 17/00*    (2006.01)

(52) U.S. Cl.
CPC ....... *A61B 17/326* (2013.01); *A61B 2017/0023* (2013.01)

(58) Field of Classification Search
CPC .... A61B 17/00; A61B 17/326; A61B 17/122; A61B 2017/0023
USPC .......................... D24/143; 606/118, 120, 151
See application file for complete search history.

(56) References Cited

U.S. PATENT DOCUMENTS

| | | | | | |
|---|---|---|---|---|---|
| 2,353,647 | A | * | 7/1944 | Carmichael | 606/118 |
| 5,269,788 | A | * | 12/1993 | Nelson, III | 606/118 |
| 7,303,567 | B1 | * | 12/2007 | Smith | 606/118 |
| 2012/0203242 | A1 | * | 8/2012 | Fuerst et al. | 606/118 |

FOREIGN PATENT DOCUMENTS

WO    WO 2005039424 A1 *    5/2005    ........... A61B 17/326

* cited by examiner

*Primary Examiner* — Ashley Fishback
(74) *Attorney, Agent, or Firm* — Gokalp Bayramoglu

(57) ABSTRACT

The present invention relates to a disposable circumcision apparatus, the apparatus comprising an inner ring (1) for placement onto a penis. The inner ring (1) is connected to one or more connecting rods (11). The inner ring (1) may comprise a slanted structure substantially conforming to the coronal sulcus of a penis. The apparatus may also comprise an outer ring for use in preventing foreskin blood circulation during circumcision surgery, the outer ring sized and shaped to match an external diameter of the inner ring. A detachment structure (14) is provided at the connection between the inner ring and the connecting rod(s) that allow the connecting rod(s) to be removed from the inner ring once the inner ring has been placed onto the penis.

20 Claims, 6 Drawing Sheets

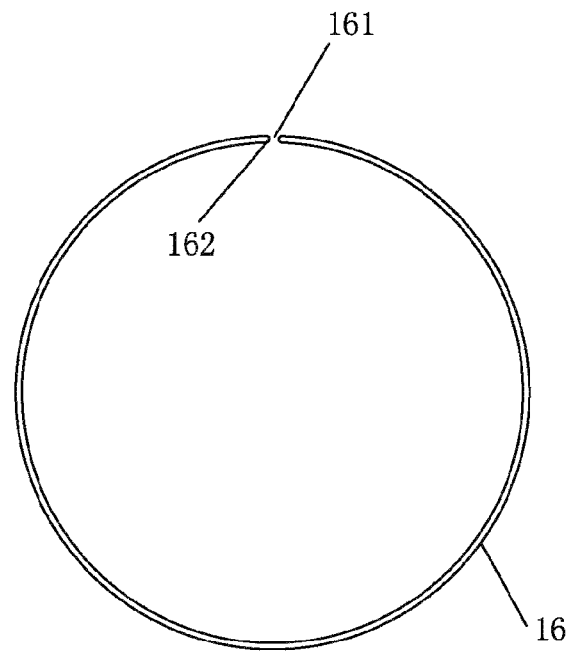
Fig 6
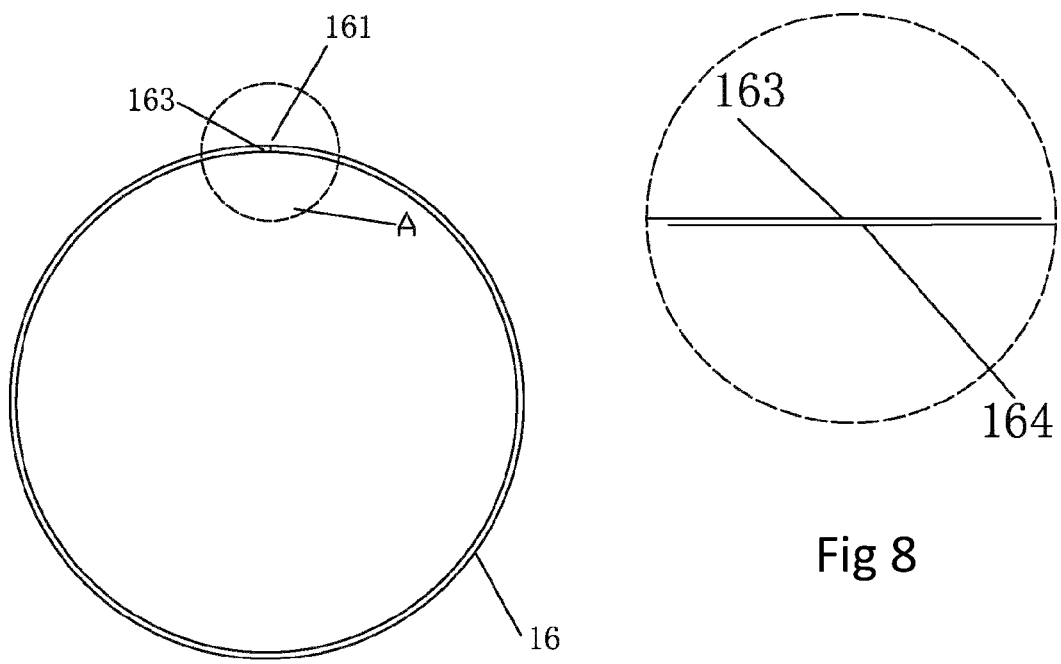
Fig 7
Fig 8

DISPOSABLE CIRCUMCISION CLAMP

CROSS REFERENCE TO RELATED APPLICATIONS

This application is the national stage of PCT application serial number PCT/CN2011/001386, filed on Aug. 19, 2011, which claims priority to Chinese application serial number 201020299303.5, filed on Aug. 20, 2010, the entire contents of which are incorporated herein.

BACKGROUND

1. Field of the Invention

The invention relates to a type of medical apparatus, and more particularly to a disposable circumcision apparatus.

2. Related Art

Redundant prepuce or phimosis is one of the reasons for male urinary system infection and aggravation of sexually transmitted diseases. Redundant prepuce or phimosis can cause urinary tract infection that may lead to chronic prostatitis, which presents as a series of symptoms such as back pain, impotence and prospermia. In addition, the effect of male circumcision has been widely recognized in reducing the transmission HIV. Therefore, removing redundant foreskin or phimosis is a good way to prevent and/or arrest these diseases.

One of the inventors of the present invention, Mr. Jianzhong Shang, has been credited by some authorities as having created key products and technologies in the field of circumcision. The development of circumcision apparatuses has now entered a new stage of design and promotion.

Current circumcision tools typically comprise an inner ring placed onto a penis, typically a small child or even an infant. The prepuce is uncovered at first and the inner ring is tied onto a corresponding location of the penis. Then the prepuce is placed over the inner ring and is tied with a ligature, so as to prevent blood circulation.

However, due to the small size of the penis in a typical circumcision procedure and the high degree of precision needed during surgery, it is difficult to properly place and secure the inner ring to the penis, possibly resulting in discomfort for patients, especially infants.

SUMMARY

The main objective of the present invention is to overcome the weakness of the prior art to provide a safer, cleaner, and more convenient apparatus for fitly circumcising a penis. In order to realize the above-mentioned objective, the present invention adopts the following technical solutions: A disposable circumcision apparatus comprising an inner ring for placement onto a penis. The inner ring comprises a slanted structure matching the coronal sulcus of the penis, and the inner ring is connected to one or more connecting rods.

In one embodiment, one connecting rod is used.

In another embodiment, two connecting rods are used, the two connecting two rods spaced apart from each other to form a space large enough to fit a penis, wherein each end of the connecting rods is attached to a handle.

In one embodiment, the inner ring comprises an elastic pad on the outside of the inner ring.

The apparatus may comprise a ligature which is placed around the inner ring, and is used to tie the prepuce.

In another embodiment, the apparatus comprise an outer ring which is sized and shaped to receive the inner ring.

In one embodiment, the outer ring comprises a C-shaped structure with an opening.

The C-shaped structure comprises two ends, each end comprising a rounded structure, wherein one end comprises an upper part and the other end comprises a lower part, the parts overlapping each other when the C-shaped structure is placed into a closed position.

In one embodiment, the inner ring comprises a V-shaped cross-section. In another embodiment, the inner ring comprises an M-shaped cross section.

In one embodiment, the connecting rod(s) is/are attached to the inner ring with a detachment structure that allows the connecting rods(s) to be removed from the inner ring.

The detachment structure comprises a score or notch in the connecting rod(s) or on the inner ring.

Advantageously, the connecting rod(s) enable a surgeon to guide the inner ring into a precise position over a penis during circumcision surgery. After placement of the inner ring, the connecting rod(s) may be removed by virtue of the detachment structure(s) in the area where the connecting rod(s) and the inner ring meet. In one embodiment, the inner ring comprises an obliquely elliptic structure corresponding to the coronary sulcus, thus providing a better fit between the coronary sulcus and the inner ring.

BRIEF DESCRIPTION OF THE DRAWINGS

FIG. 6 is a structural illustration of an outer ring in an open position.

FIG. 7 is a structural illustration of the outer ring of FIG. 6 in a closed position.

FIG. 8 is an enlarged view of Part A in FIG. 7.

DETAILED DESCRIPTION

Figure 1:
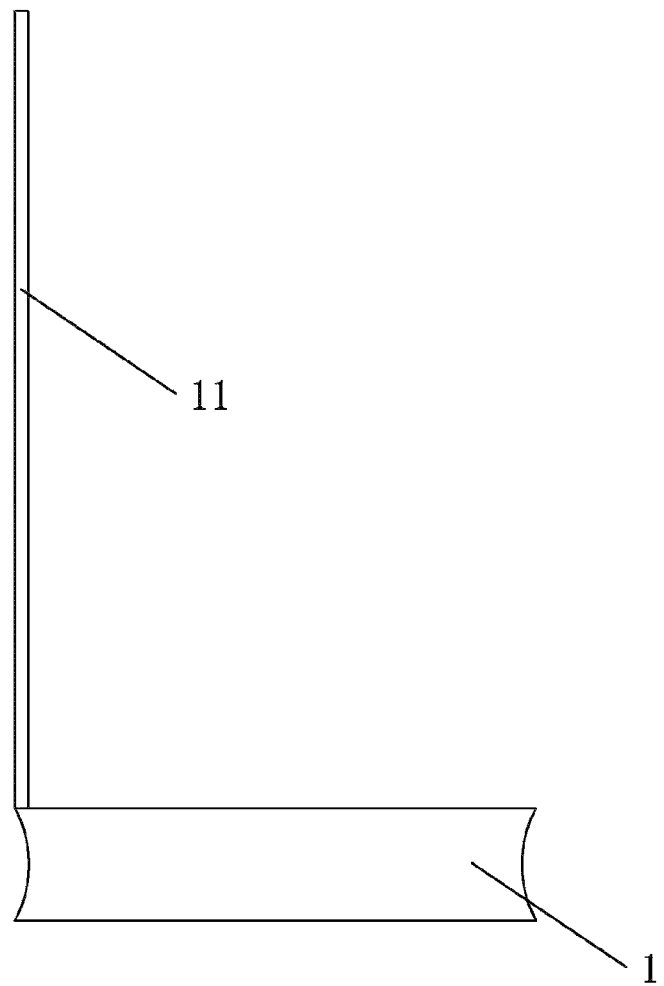
FIG. 1 is a side view of a first embodiment of a disposable circumcision apparatus.

The present invention relates to a disposable circumcision apparatus. As shown in FIG. 1, in a first embodiment, a disposable circumcision apparatus comprises an inner ring 1, which is attached to a single connecting rod 11. In other embodiments, more than one connecting rod may be used. The connecting rod 11 can be used by a surgeon during circumcision surgery to guide the inner ring into a precise position over a penis, thereby making the procedure easier for the surgeon.

Figure 2:
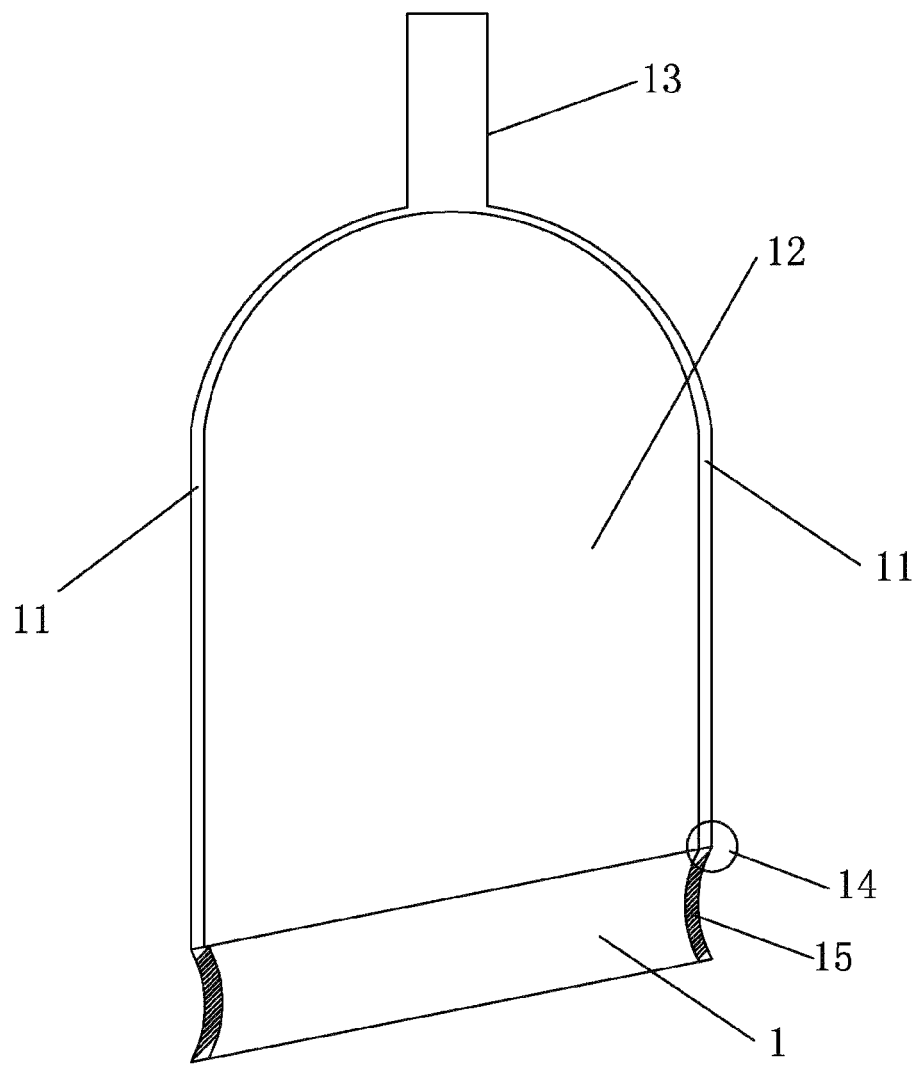
FIG. 2 is a side, cut-away view of a second embodiment of a disposable circumcision apparatus.

FIG. 2 is a side view of a second embodiment of a disposable circumcision comprises two connecting rods 11 spaced apart from one another to form a space 12 large enough to accommodate a penis. Thus, the inner ring will not touch the glans while being placed onto the penis. Each end of the connecting rods is attached to the inner ring, while each of the other ends is connected to a handle 13, making the structure stronger and more robust.

The disposable circumcision apparatus may be made of plastics. Thus, the connecting rod(s) can be broken away from the inner ring after placement of the inner ring onto the penis.

Figure 3:
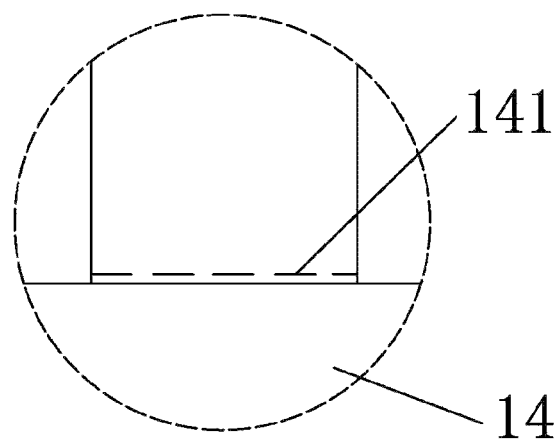
FIG. 3 is an enlarged view of one embodiment of a detachment structure.
Figure 4:
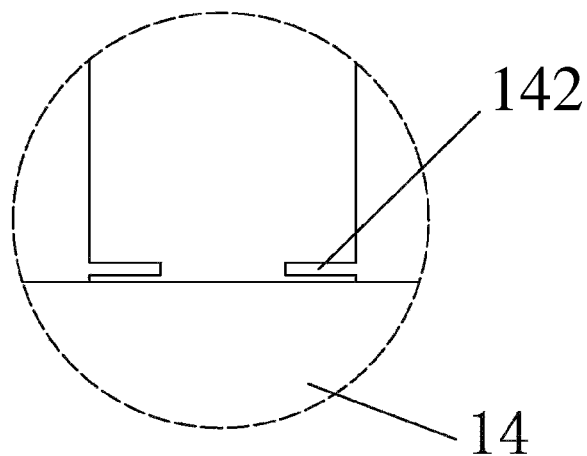
FIG. 4 is the enlarged view of another embodiment of a detachment structure.

In another embodiment, as shown in FIG. 2, a detachment structure 14 is arranged at the joint between inner ring 1 and the connecting rods 11, so that the connecting rods may be more easily detached from the inner ring. Thus, detachment structure 14 reduces the rigidity of connecting rod 11. As shown in FIGS. 3 and 4, the detachment structure may comprise a score 141 or notch 142 in the connecting end(s) proximate to the inner ring. In other embodiments, other forms of detachment structures may be used.

As shown in FIG. 2, the inner ring 1 can comprise an obliquely elliptic structure corresponding to the coronary sulcus, thus providing a better fit between the coronary sulcus and the inner ring. An elastic pad 15, such as a rubber pad, can be arranged around the exterior surface of inner ring 1, forming a soft surface against which the prepuce is in contact, thus reducing discomfort experienced by patients.

Figure 5:
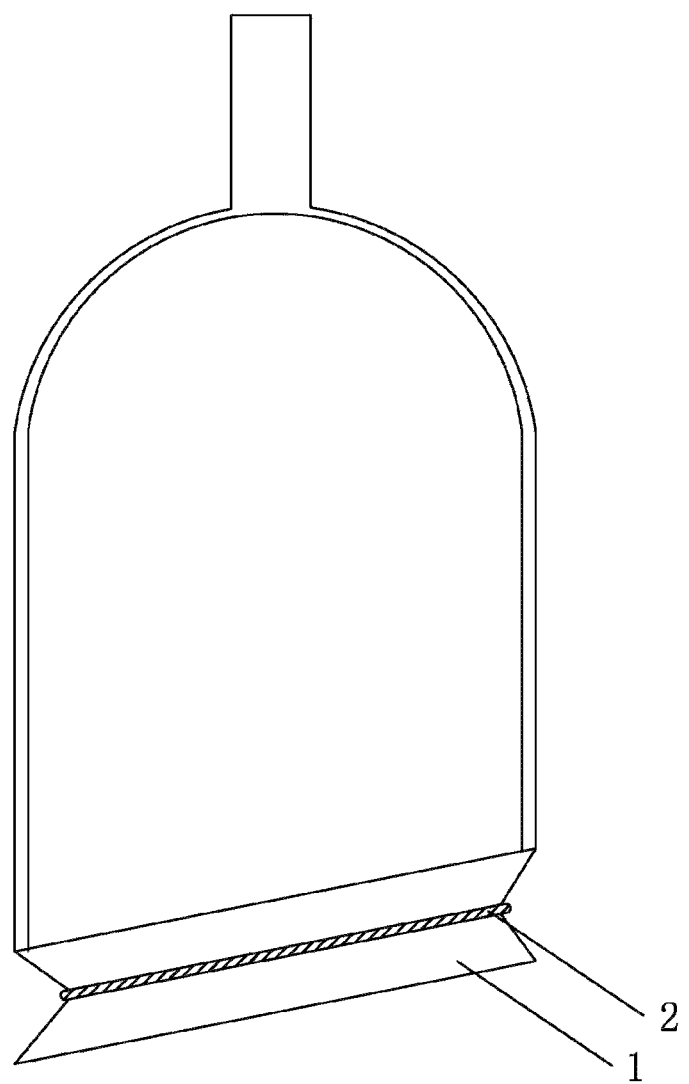
FIG. 5 is a side view of a third embodiment of a disposable circumcision apparatus.

FIG. 5 illustrates another embodiment of the present invention. In this embodiment, the disposable circumcision apparatus further comprises ligature 2 and the inner ring 1 comprises a V-shaped cross-section. In operation, the prepuce wraps around the inner ring 1 and ligature 2 is tied around the prepuce over the center of the V-shaped cross-section. This prevents blood circulation in the portion of the prepuce after the ligature. The V-shaped cross-section can better position the ligature 2 and helps prevent movement of the ligature with respect to the prepuce.

In one embodiment, the ligature may be replaced by an outer ring for preventing blood circulation of the prepuce. The outer ring comprises a diameter that is similar to the diameter of the inner ring 1 around its center. The outer ring may comprise an outer ring used in present disposable circumcision apparatuses.

As shown in FIG. 6, the outer ring comprises a C-shaped ring 16 with an opening 161. As shown in FIGS. 6, 7, and 8, the C-shaped structure 16 comprises two ends, each end comprising a rounded structure 162, wherein one end comprises an upper part 163 and the other end comprises a lower part 164, the parts overlapping each other when the C-shaped structure 16 is placed into a closed position, as best shown in in the close-up view of FIG. 8. The rounded structure of the ends and the overlapped parts prompt the steel ring not to interfere with blood circulation of the prepuce while closed.

Figure 9:
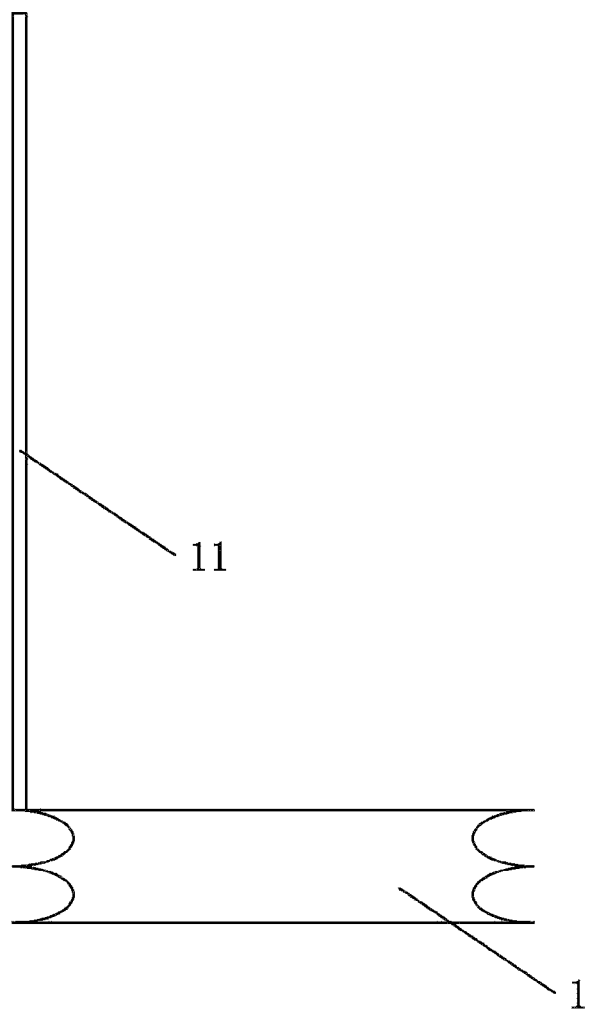
FIG. 9 is a side view of a fourth embodiment of a disposable circumcision apparatus.

FIG. 9 illustrates yet another embodiment of a disposable circumcision apparatus. In this embodiment, the inner ring comprises an M-shaped cross-section, so as to match with an outer ring comprising an annular, dual-blade structure. Of course, the inner ring may, alternatively, utilize the C-shaped structure 16, a ligature, etc.

The parts that comprise the disposable circumcision apparatus as described herein can either be sold separately (e.g. the ligature may comprise a medial ligature that is commonly sold independently), or as a package (e.g. together with the C-shaped ring or outer ring), which are at a customer's discretion.

With respect to the above description, it is to be realized that the optimum dimensional relationships of the various components include variations in size, materials, shape, form, function and manner of operation, assembly and use, and are deemed readily apparent and obvious to one skilled in the art. All equivalent relationships to those illustrated in the drawings and described in the specification are intended to be encompassed by the embodiments described herein. Therefore, the foregoing is considered as illustrative only of the principles and descriptions provide herein. Further, since numerous modifications and changes may be contemplated by those skilled in the art, it is not desired to limit the embodiments described herein to the exact construction and operation shown and described, and accordingly, all suitable modifications and equivalents may be resorted to, falling within the scope of the present disclosure.

We claim:

1. A disposable circumcision apparatus, comprising:
an inner ring sized and shaped to fit on a penis having:
a first connecting rod detachably connected to the inner ring;
a detachment structure formed at the connection between the inner ring and a first end of the connecting rod for allowing the first connecting rod to be permanently detached from the inner ring, wherein the detachment structure is a notch;
an outer ring for removable placement over the inner ring;
wherein a rubber pad is arranged around the exterior surface of the inner ring;
wherein the inner ring comprises an oblique angle with respect to the first connecting rod, matching the coronal sulcus of a penis for providing a better fit between the coronary sulcus and the inner ring; wherein the inner ring comprises a V-shaped groove.

2. The apparatus as claimed in claim 1, further comprising:
a second connecting rod;
wherein the first and second connecting rods form a space to contain the penis, each of the rods connected to a handle.

3. The apparatus as claimed in claim 1, wherein:
the apparatus comprises a string which matches with the inner ring used for tying the prepuce.

4. The apparatus claimed in claim 1, wherein:
the outer ring comprises a C-shaped steel ring, comprising a first end and a second end forming an opening when the C-shaped steel ring is in an open position.

5. The apparatus as claimed in claim 4, wherein:
the first end and the second end each comprises a rounded structure, and upper and lower parts which overlap each other when the C-shaped steel ring is in a closed position.

6. A disposable circumcision apparatus, comprising:
an inner ring sized and shaped to fit on as penis having:
a first connecting rod detachably connected to the inner ring;
a detachment structure formed at the connection between the inner ring and a first end of the connecting rod for allowing the first connecting rod to be permanently detached from the inner ring, wherein the detachment structure is a score;
an outer ring for removable placement over the inner ring;
wherein as rubber pad is arranged around the exterior surface of the inner ring;
wherein the inner ring comprises an oblique angle with respect to the first connecting rod, matching the coronal sulcus of a penis for providing a better fit between the coronary sulcus and the inner ring; wherein the inner ring comprises a V-shaped groove.

7. The apparatus as claimed in claim 6, further comprising:
a second connecting rod;
wherein the first and second connecting rods form a space to contain the penis, each of the rods connected to a handle.

8. The apparatus as claimed in claim 6, wherein:
the apparatus comprises a string which matches with the inner ring used for tying the prepuce.

9. The apparatus claimed in claim 6, wherein:
the outer ring comprises a C-shaped steel ring, comprising a first end and a second end forming an opening when the C-shaped steel ring is in an open position.

10. The apparatus as claimed in claim 9, wherein:
the first end and the second end each comprises a rounded structure, and upper and lower parts which overlap each other when the C-shaped steel ring is in a closed position.

11. A disposable circumcision apparatus, comprising:
an inner ring sized and shaped to fit on a penis having:
- a first connecting rod detachably connected to the inner ring;
- a detachment structure formed at the connection between the inner ring and a first end of the connecting rod for allowing the first connecting rod to be permanently detached from the inner ring, wherein the detachment structure is a notch;

an outer ring for removable placement over the inner ring;
wherein a rubber pad is arranged around the exterior surface of the inner ring;
wherein the inner ring comprises an oblique angle with respect to the first connecting rod, matching the coronal sulcus of a penis for providing a better fit between the coronary sulcus and the inner ring; wherein the inner ring comprises an M-shaped groove for receiving an annular, double-blade outer ring.

12. The apparatus as claimed in claim 11, further comprising:
a second connecting rod;
wherein the first and second connecting rods form a space to contain the penis, each of the rods connected to a handle.

13. The apparatus as claimed in claim 11, wherein:
the apparatus comprises a string which matches with the inner ring used for tying the prepuce.

14. The apparatus claimed in claim 11, wherein:
the outer ring comprises a C-shaped steel ring, comprising a first end and a second end forming an opening when the C-shaped steel ring is in an open position.

15. The apparatus as claimed in claim 14, wherein:
the first end and the second end each comprises a rounded structure, and upper and lower parts which overlap each other when the C-shaped steel ring is in a closed position.

16. A disposable circumcision apparatus, comprising:
an inner ring sized and shaped to fit on a penis having:
- a first connecting rod detachably connected to the inner ring;
- a detachment structure formed at the connection between the inner ring and a first end of the connecting rod for allowing the first connecting rod to be permanently detached from the inner ring, wherein the detachment structure is a score;

an outer ring for removable placement over the inner ring;
wherein a rubber pad is arranged around the exterior surface of the inner ring;
wherein the inner ring comprises an oblique angle with respect to the first connecting rod, matching the coronal sulcus of a penis for providing a better fit between the coronary sulcus and the inner ring; wherein the inner ring comprises a M-shaped groove for receiving an annular, double-blade outer ring.

17. The apparatus as claimed in claim 16, further comprising:
a second connecting rod;
wherein the first and second connecting rods form a space to contain the penis, each of the rods connected to a handle.

18. The apparatus as claimed in claim 16, wherein:
the apparatus comprises a string which matches with the inner ring used for tying the prepuce.

19. The apparatus claimed in claim 16, wherein:
the outer ring comprises a C-shaped steel ring, comprising a first end and a second end forming an opening when the C-shaped steel ring is in an open position.

20. The apparatus as claimed in claim 19, wherein:
the first end and the second end each comprises a rounded structure, and upper and lower parts which overlap each other when the C-shaped steel ring is in a closed position.

* * * * *